US007034130B2

(12) United States Patent
Jeschke et al.

(10) Patent No.: US 7,034,130 B2
(45) Date of Patent: Apr. 25, 2006

(54) METHOD FOR PRODUCING NOVEL SPINOSYN DERIVATIVES

(75) Inventors: Peter Jeschke, Bergisch Gladbach (DE); Günther Eberz, Odenthal (DE); Rita Fröde, Cary, NC (US); Volker Möhrle, Köln (DE); Robert Velten, Köln (DE)

(73) Assignee: Bayer Cropscience AG, Monheim (DE)

( * ) Notice: Subject to any disclaimer, the term of this patent is extended or adjusted under 35 U.S.C. 154(b) by 0 days.

(21) Appl. No.: 10/483,543

(22) PCT Filed: Jul. 8, 2002

(86) PCT No.: PCT/EP02/07572

§ 371 (c)(1), (2), (4) Date: Jul. 9, 2004

(87) PCT Pub. No.: WO03/010155

PCT Pub. Date: Feb. 6, 2003

(65) Prior Publication Data

US 2004/0242858 A1 Dec. 2, 2004

(30) Foreign Application Priority Data

Jul. 20, 2001 (DE) ................................ 101 35 550

(51) Int. Cl.
*C07H 17/08* (2006.01)

(52) U.S. Cl. ...................................... 536/7.1; 536/18.1

(58) Field of Classification Search .................. 435/76; 536/7.1, 18.1
See application file for complete search history.

(56) References Cited

U.S. PATENT DOCUMENTS 2,864,837 A 12/1958 Sebek et al. ........... 260/397.45
4,217,416 A 8/1980 Daumy ....................... 435/146
4,666,937 A 5/1987 Goegelman et al. ......... 514/450
5,132,228 A 7/1992 Lobos et al. ............. 435/252.1
5,202,242 A 4/1993 Mynderse et al. ............ 435/76
5,362,634 A 11/1994 Boeck et al. ................. 435/76
5,496,931 A 3/1996 Boeck et al. ................ 536/7.1
5,539,089 A 7/1996 Broughton et al. .......... 536/6.5
5,571,901 A 11/1996 Boeck et al. ................ 536/7.1
5,670,364 A 9/1997 Mynderse et al. ....... 435/252.1
5,670,486 A 9/1997 Mynderse et al. ............ 514/28
5,756,536 A 5/1998 Chen et al. ................. 514/449
5,840,861 A 11/1998 Mynderse et al. ......... 536/16.8
5,879,916 A 3/1999 De-Eknamkul et al. ..... 435/155
5,972,994 A 10/1999 Shafiee et al. .............. 514/450
6,162,622 A 12/2000 Hanson et al. .............. 435/123
6,455,504 B1 9/2002 Lewer et al. ................. 514/28
6,664,237 B1 12/2003 Snyder ........................ 514/28
2003/0186899 A1 10/2003 Lewer et al. ................. 514/28

FOREIGN PATENT DOCUMENTS

CA 2 379 331 2/2001
WO 97/00265 1/1997
WO 01/11962 2/2001
WO 01/16303 3/2001

OTHER PUBLICATIONS

Tetrahedron, vol. 32, No. 37, (month unavailable) 1991, pp. 4839-4842, Herbert A. Kirst et al "A83543A-D, Unique Fermentation-Derived Tetracyclic Macrolides".

Pesticide Manual, British Crop Protection Council, 11th ed., (month unavailable) 1997, pp. 1272-1273, XDE-105.

J. Org. Chem. 59, (month unavailable) 1994, pp. 1548-1560, Jacek G. Martynow et al, "Chemistry of A83543A Derivatives. 1. Oxidations and Reductions of A83543A Aglycon".

J. Econ. Entomol.,, 91(6), Dec. 1998, pp. 1277-1283, T.C. Sparks et al, Biological Activity of the Spinosyns, New Fermentation Derived Insect Control Agents, on Tobacco Budworm (Lepidoptera: Noctuidae) Larvae.

Pestic. Biochem. Physiol. 67, (month unavailable) 2000, pp. 187-197, Thomas C. Sparks et al, "The Application of Artificial Neural Networks to the Identification of New Spinosoids with Improved Biological Activity toward Larvae of *Heliothis virescens*".

J. Am. Chem. Soc., 120 (month unavailable) 1998, pp. 2553-2562, Leo A. Paquette et al, "Total Synthesis of Spinosyn A. 2. Degradation Studies Involving the Pure Factor and its Complete Reconstitution".

Pest. Manag. Sci. 57 (2), (month unavailable) 2001, pp. 177-185, Gary D. Crouse et al, "Recent advances in the chemistry of spinosyns".

J. Antibiotics 53(2), Feb. 2000, pp. 171-178, Lawrence C. Creemer et al, "Synthesis and Insecticidal Activity of Spinosyn Analogs Functionally Altered at the 2'-,3'-and 4'-Position of the Rhamnose Moiety".

Proc. Beltwide Cotton Conf., vol. 2, (month unavailable) 2000, pp. 1225-1229, Thomas C. Sparks et al, "Structure Activity Relationships of the Spinosyns".

J. Antitbiotics, vol. 51, No. 8, (month unavailable) 1998, pp. 795-800, Lawrence C. Creemer er al, "Conversion of Spinosyn A and Spinosyn D to Their Respective 9- and 17-Pseudoaglycones and Their Aglycones".

Down to Earth-Down Elanco trade magazine, vol. 52, No. 1(month unavailable) 1997, pp. 1-43.

*Primary Examiner*—Elli Preselev
(74) *Attorney, Agent, or Firm*—Richard E. L. Henderson; Raymond J. Harmuth

(57) ABSTRACT

The present invention relates to methods for producing novel spinosyn derivatives which are substituted with a 1-hydroxy-ethyl radical in the C-21 position and to novel spinosyn derivatives of this type per se and to their use for producing novel spinosyns.

5 Claims, No Drawings

METHOD FOR PRODUCING NOVEL SPINOSYN DERIVATIVES

CROSS-REFERENCE TO RELATED APPLICATIONS

The present application is the national phase of PCT Application Ser. No. PCT/EP02/07572, filed Jul. 8, 2002, which claimed priority to German Application No. 101 35 550.5, filed Jul. 20, 2001.

The present invention relates to methods for producing novel spinosyn derivatives which are substituted with a 1-hydroxy-ethyl radical in the C-21 position and to novel spinosyn derivatives of this type per se and to their use for producing novel spinosyns.

The spinosyns are known compounds. Spinosyns are fermentation products which are produced by cultures of the actinomycetes *Saccharopolyspora spinosa*. Natural spinosyns consist of a tetracyclic polyketide backbone (aglycone) with a 12-membered macrolide ring and a 5,6,5-cis-anti-trans-tricycle and also a D-forosamine and a 2,3,4-tri-O-methyl-L-rhamnose sugar moiety (Kirst et al., 1991, Tetrahedron Letters, 32:4839). More than 20 different natural spinosyns, the "A83543 complex", have been described previously (cf. WO 97/00265, WO 94/20518 and WO 93/09126). EP-A 375316, for example, describes the spinosyns A, B, C, D, E, F, G, H and J. WO 93/09126 discloses the spinosyns L, M, N, Q, R, S and T. The spinosyns K, O, P, U, V, W and Y and their derivatives are mentioned in WO 94/20518. These compounds vary in the substitution of one or more methyl groups on the tetracyclic backbone, on the D-forosamine sugar moiety or on the 2,3,4-tri-O-methyl-L-rhamnose sugar moiety. A 17-pseudoaglycone which reacts the D-forosamine sugar moiety has likewise been isolated from *S. spinosa* culture broth.

The main components of the A83543 complex produced by *S. spinosa* are the variants spinosyn A and spinosyn D which are the essential components of the product spinosad (cf. Pesticide Manual, British Crop Protection Council, 11th Ed., 1997, page 1272 and Dow Elanco Trade Magazine Down to Earth, Vol. 52, NO. 1, 1997 and the literature quoted therein).

If the amino sugar in the C-17 position is not present, the compounds are referred to as spinosyn A, D, etc. 17-pseudoaglycone; if the neutral sugar in the C-9 position is not present, the compounds are referred to as spinosyn A, D, etc. 9-pseudoaglycone. Spinosyns without the two sugar residues in the positions C-9 and C-17 are referred to as spinosyn aglycone.

Spinosyns are suitable for controlling arachnids, nematodes, ectoparasites (cf. WO 01/11962, WO 01/11963, WO 01/11964) and insects, in particular *Lepidoptera* and *Diptera* species. In addition, technical application of the spinosyns is environmentally sound and, moreover, this substance class has an attractive toxicological profile.

However, animal pests, in particular ectoparasites, or plant pests which are currently controlled using spinosyns can be expected to be able to develop a resistance to these commercially available active substances. It is therefore important to produce novel biologically active spinosyn derivatives which can replaced the spinosyns currently used for controlling pests.

Recently, *Saccharopolyspora* sp. (LW107129) has been used to generate specific natural aglycone derivatives of spinosyn which have a hydroxyl group in the C-8 position of the macrolide backbone and which have become known as insecticidal compounds (cf. WO 0.01/19840). While numerous modifications of spinosyns have been carried out (cf. WO 97/00265), derivatizations on the methyl group and ethyl group in the C-21 position of the macrolide backbone drew only little attention. Although functionalization of the alkyl radical in the C-21 position would be advantageous, inter alia for derivatization reactions, only few spinosyn derivatives are known whose substituents have a hydroxyl group in C-21. For example, only recently have spinosyn derivatives been described which are substituted in C-21 with a 3-hydroxy-1-butenyl radical, which may, where appropriate, additionally carry a hydroxyl group in the abovementioned C-8 position and which have an insecticidal action (cf. WO 01/19840).

While chemical synthesis methods for preparing spinosyn derivatives have been described (cf. Martynow, J. G. and Kirst, H. A., 1994, J. Org. Chem., 59: 1548), there has up until now been no knowledge about chemical synthesis of the above-mentioned spinosyn derivatives having a 1-hydroxy-ethyl radical in the C-21 position.

It is the object of the present invention to provide suitable methods which may be used for the selective and/or stereospecific production of novel spinosyn derivatives having a 1-hydroxy-ethyl radical in the C-21 position.

The object was achieved by providing methods for producing compounds of the general formula (I), (I)

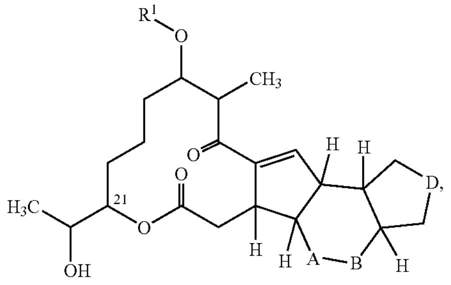

in which

A-B is any of the following groups: —HC═CH—, —HC═C($CH_3$)—, —$H_2C$—$CH_2$— or —$H_2C$—CH($CH_3$)—;

D is the group

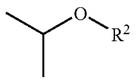 or 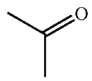, $R^1$ is hydrogen or an amino sugar and $R^2$ is hydrogen or a sugar, in which compounds of the general formula (II),

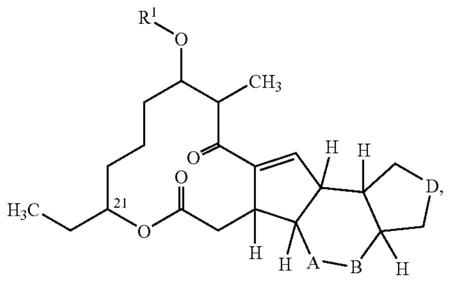

(II)

in which

A-B, D and $R^1$ are as defined above, are contacted with a microorganism in an aqueous nutrient medium under aerobic conditions or with an enzyme extract prepared therefrom or with one or more enzymes isolated therefrom.

The starting compounds are thus selectively and/or stereospecifically converted to spinosyn derivatives substituted in the C-21 position by a 1-hydroxy-ethyl radical by means of biotransformation using microorganisms or their enzymes.

The term "spinosyn derivatives", as used herein, also comprises spinosyn aglycone compounds, i.e. compounds which have the macrolide backbone of the spinosyns but no sugar radicals.

Preference is given to using as starting compounds those compounds of the general formula (II)

in which, in the case (1) that

A-B is any of the following groups: $-HC{=}CH-$, $-HC{=}C(CH_3)-$, $-H_2C-CH_2-$ or $-H_2C-CH(CH_3)-$ and D is the group

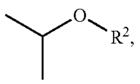

$R^1$ is an amino sugar of the formula 1a

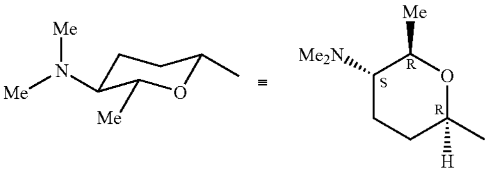

1a and $R^2$ is a sugar of the formula 2a

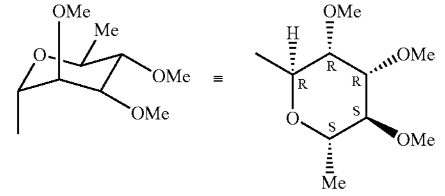

2a or in which, in the case (2) that

A-B is the group $-HC{=}CH-$ or $-H_2C-CH_2-$ and

D is as defined above, $R^1$ is an amino sugar of the abovementioned formula 1a and $R^2$ is hydrogen or a sugar of the formula 2b, 2c, 2d, 2e or 2f

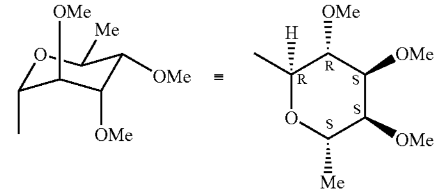

2b

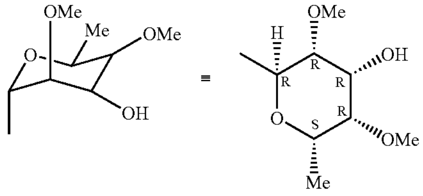

2c

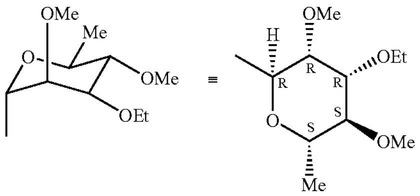

2d

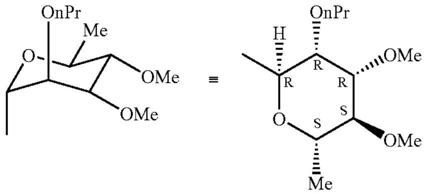

2e

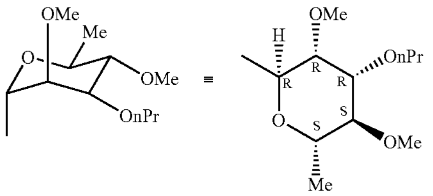

2f or in which, in the case (3) that

A-B is any of the following groups: $-HC{=}CH-$, $-HC-C(CH_3)-$ or $-H_2C-CH_2-$ and D is as defined above, $R^1$ is hydrogen or an amino sugar of the formula 1b 1b

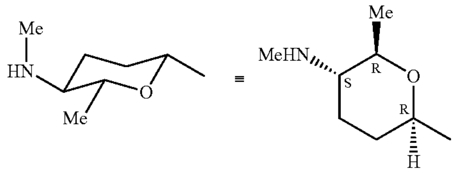

and $R^2$ is hydrogen or a sugar of the abovementioned formula 2a or in which, in the case (4) that A-B is the group —HC═CH— or —HC═C($CH_3$)— and D is as defined above, $R^1$ is an amino sugar of the abovementioned formula 1a and $R^2$ is a sugar of the formula 2g, 2h, 2i, 2j or 2k 2g

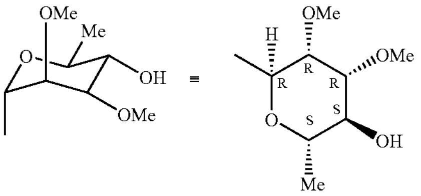

2h

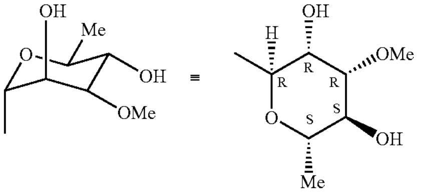

2i

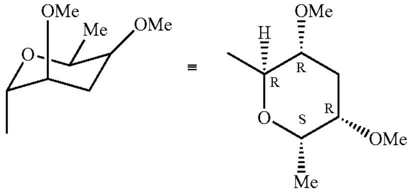

2j

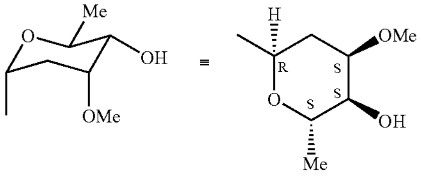

2k

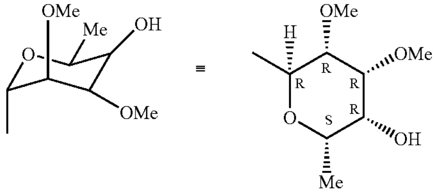

or in which, in the case (5) that

A-B is the group —HC═CH— or —$H_2C$—$CH_2$— and

D is as defined above, $R^1$ is an amino sugar of the abovementioned formula 1a and $R^2$ is a sugar of the formula 2l or 2m 2l

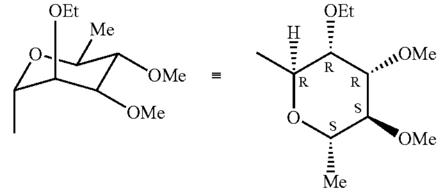

2m

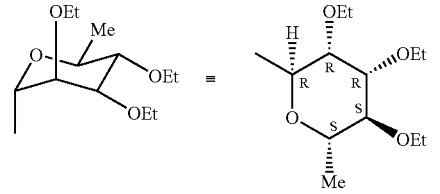

or in which, in the case (6) that

A-B is the group —HC═CH— or —HC═C($CH_3$)— and

D is as defined above, $R^1$ is hydrogen or an amino sugar of the abovementioned formula 1b or an amino sugar of the formula 1c 1c

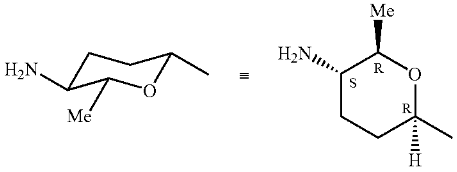

and $R^2$ is a sugar of the abovementioned formula 2b, 2c, 2g or 2h or a sugar of the formula 2n 2n

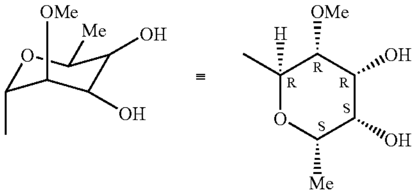

or in which, in the case (7) that

A-B is the group —HC═CH— and

D is as defined above, $R^1$ is an amino sugar of the abovementioned formula 1a and $R^2$ is a sugar of the formula 2o 2o

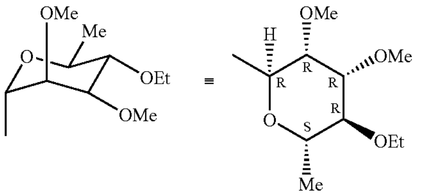

or in which, in the case (8) that
A-B is the group —HC═CH— and
D is as defined above,
$R^1$ is an amino sugar of the abovementioned formula 1b and
$R^2$ is a sugar of the abovementioned formula 2d, 2i or 2j or a sugar of the formula 2p 2p

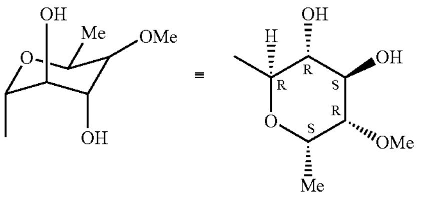

or in which, in the case (9) that
A-B is the group —HC═CH— and
D is as defined above,
$R^1$ is hydrogen or an amino sugar of the abovementioned formula 1c and
$R^2$ is a sugar of the abovementioned formula 2i or 2p, or in which, in the case (10) that
A-B is the group —HC═CH— and
D is as defined above,
$R^1$ is an amino sugar of the formula 1d, 1e or 1f 1d

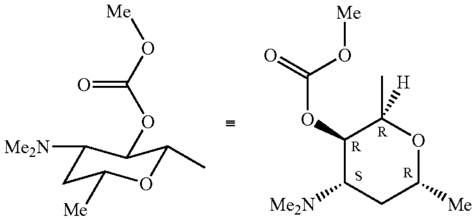

1e

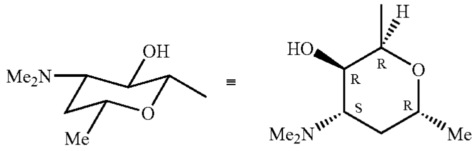

1f

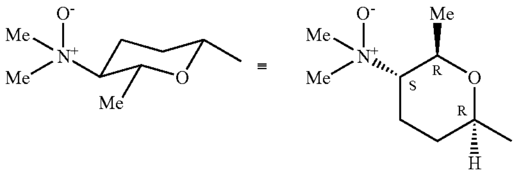

and
$R^2$ is a sugar of the abovementioned formula 2a or in which, in the case (11) that
A-B is the group —HC═CH— and
D is the group

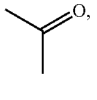

$R^1$ is hydrogen or an amino sugar of the abovementioned formula 1a.

Particular preference is given to using as starting compounds those compounds of the general formula (II)

in which, in the case (12) that
A-B is the group —HC═CH— or —HC═C($CH_3$)— and
D is the group

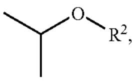

$R^1$ is an amino sugar of the formula 1a and
$R^2$ is a sugar of the formula 2a, 2g or 2h or in which; in the case (13) that
A-B is the group —HC═CH— and
D is as defined above,
$R^1$ is an amino sugar of the formula 1a and
$R^2$ is hydrogen or a sugar of the formula 2d, 2e, 2l, 2m or 2o or in which, in the case (14) that
A-B is the group —HC═CH— or —HC═C($CH_3$)— and
D is as defined above,
$R^1$ is hydrogen or an amino sugar of the formula 1b and
$R^2$ is hydrogen or a sugar of the formula 2a or in which A-B, D and $R^1$ are as defined in the case (11).

Very particular preference is given to using as starting compounds compounds of the general formula (II)

in which, in the case (15) that
A-B is the group —HC═CH— or —HC═C($CH_3$)— and
D is the group

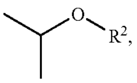

$R^1$ is an amino sugar of the formula 1a and
$R^2$ is a sugar of the formula 2a or in which, in the case (16) that
A-B is the group —HC═CH— and
D is as defined above,
$R^1$ is an amino sugar of the formula 1a and
$R^2$ is hydrogen or a sugar of the formula 2d, 2l or 2m or in which A-B, D and $R^1$ are as defined in the case (11).

Most preference is given to using as starting compounds compounds of the general formula (II)

in which, in the case (17) that
A-B is the group —HC═CH— or —HC═C($CH_3$)— and
D is the group

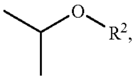

$R^1$ is an amino sugar of the formula 1a and
$R^2$ is a sugar of the formula 2a or in which, in the case (18) that
A-B is the group —HC—CH— and
D is as defined above, $R^1$ is hydrogen and $R^2$ is hydrogen.

The present invention also relates to the compounds of the general formula (I) in which A-B, D and $R^1$ are as defined above.

The abbreviation "Me" used herein represents methyl; the abbreviation "Et" represents ethyl.

The method of the invention may be used to form the optically active, stereoisomeric forms but also diastereomeric forms of the compounds of the general formula (I).

The compounds of the invention of the formula (I) can exist in stereoisomeric forms which either behave as image and mirror image (enantiomers) or which do not behave as image and mirror image (diastereomers). The present invention relates to both the enantiomers and the diastereomers and to the respective mixtures thereof. The racemic forms, as well as the diastereomers can be resolved into the stereoisomerically uniform components in the known manner. Where appropriate, methods known per se can be used to interconvert said isomers.

The compounds of the invention, in which $R^1$ is an amino sugar of the formulae 1a–1e, may form salts. Salts are formed according to the standard methods for preparing salts. For example, the compounds of the invention are neutralized with appropriate acids in order to produce acid addition salts. Representatively usable acid addition salts are salts which form, for example, due to a reaction with other inorganic acids such as, for example, sulfuric acid, hydrochloric acid, hydrobromic acid, phosphoric acid, or organic carboxylic acids such as acetic acid, trifluoroacetic acid, citric acid, succinic acid, lactic acid, formic acid, maleic acid, camphoric acid, phthalic acid, glycolic acid, glutaric acid, stearic acid, salicylic acid, sorbic acid, cinnamic acid, picric acid, benzoic acid, or organic sulfonic acids such as methanesulfonic acid and para-toluenesulfonic acid, or with basic amino acids such as aspartic acid, glutamic acid, arginine, or the like.

The compounds of the general formula (II), which may be used as starting compounds for the method of the invention, have been described (cf. Creemer L. C. et al., 1998, J. Antibiotics 51 (8): 795–800; Sparks T. C. et al., 1998, J. Econ. Entomol. 91 (6): 1277–1283; Sparks T. C. et al., 2000, Pestic. Biochem. Physiol. 6.7 (3): 187–197; Paquette L. A. et al., 1998, J. Am. Chem. Soc. 120 (11): 2553–2563; Evans D. A. et al., 1993, J. Am. Chem. Soc. 115 (11): 4497–4513; Crouse G. D. et al., 2001, Pest. Manag. Sci. 57 (2): 177–185; Creemer L. C. et al., 2000, J. Antibiotics 53 (2): 171–178; Sparks T. C. et al., 2000, Proc.-Beltwide Cotton Conf. Vol. 2: 1225–1229) or may be prepared according to the method described in WO 01/16303. Similarly, the starting compounds usable for the method of the invention may be obtained starting from the appropriate natural spinosyns.

When using, for example, the spinosyn A aglycone of the formula (IIa), the method of the invention can be represented by the following reaction scheme 1:

Reaction scheme 1

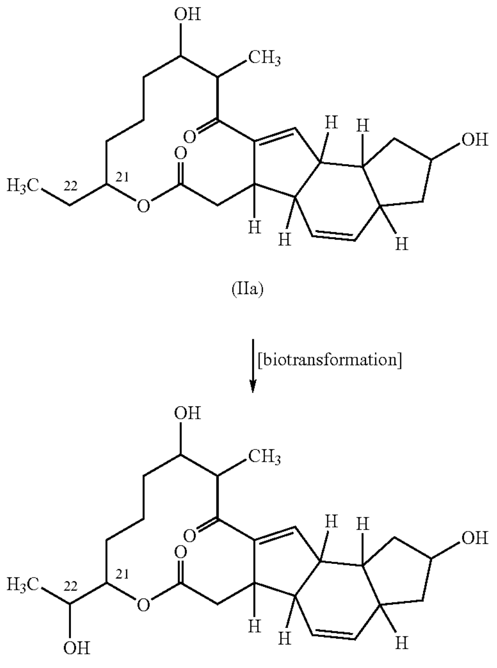

(IIa)

(Ia)

Selective and/or stereospecific hydroxylations of natural products and of synthetic compounds by bioconversion using microorganisms or their enzymes have been described in the literature. Use was made, in particular, of cells and/or enzymes of Gram-positive bacteria such as streptomycetes or Gram-negative bacteria such as *Pseudomonas* or fungi such as *Fusarium*. Examples of microorganisms containing appropriate enzyme classes such as, for example, P-450 monooxygenases are listed in the following table:

| Organism/enzyme | Chemical compound class | Reference |
|---|---|---|
| *Streptomyces halstedii* | Hydroxylation of galbonolides A and B | U.S. Pat. No. 5972994 |
| *Streptomyces* sp. MA 7065 | Hydroxylation of Taxol and cephalomannines | U.S. Pat. No. 5756536 |
| *Streptomyces roseochromogenes* (Waksman collection 3689), *Streptomyces* sp. (ATCC 11009), and *Streptomyces roseochromogenes* (ATCC 3347) | Hydroxylation of 11-oxo- or 11β-hydroxy-6α-methylprogesterone to the 16α-hydroxy derivative which is then acetylated | U.S. Pat. No. 2864837 |
| *Nocardioides luteus* | 6-Hydroxy-7-deoxytaxanes | U.S. Pat. No. 6162622 |
| *Fusarium moniliforme* | Preparation of 7α-hydroxyl derivatives from dehydroepiandrosterone and pregnenolone | FR-A 2771105 |

-continued

| Organism/enzyme | Chemical compound class | Reference |
|---|---|---|
| *Beauveria bassiana* | 2-phenoxypropionic acid | WO 95/29249 |
| *Cunninghamella blakesleena* (ATCC 8688a) | Hydroxylation of avermectin | U.S. Pat. No. 4666937 EP-A 194125 |
| *Pseudomonas testosteroni* ATCC 31492 | m-Hydroxybenzoate is transformed to give 2,3-dihydroxybenzoate | U.S. Pat. No. 4217416 |
| *Mortierella maculata* | Preparation of pravastatin, starting from compactin | WO 00/46175 |
| NADPH cytochrome-P450 reductase of plants | Hydroxylation of various substrates | WO 93/21326 |
| Bacterium NRRL-B-18737 | Preparation of bisphenol alkyl alcohols, starting from bisphenol alkanes | U.S. Pat. No. 5132228 |
| *Pseudomonas mendocina* kr-1 monooxygenase genes | Bioconversion of a phenyl compound to a phenolic compound | WO 89/09828 |
| Microorganisms or enzymes | Preparation of optically active 3-hydroxy-pyrrolidines | WO 00/29606 |
| Recombinant *Yarrowia lipolytica* expressing heterologous cytochrome-P450 systems | Bioconversion of progesterone to 17α-hydroxyprogesterone | WO 00/03008 |
| Geranylgeraniol-18-hydroxylase purified from *Croton sublyratus* | Bioconversion of geranylgeraniol to plaunotol | U.S. Pat. No. 5879916 |

According to the invention and to the abovementioned reaction scheme 1, it is possible to contact compounds of the general formula (II in which A-B, D and $R^1$ are as defined above with a suitable microorganism in an aqueous nutrient medium under aerobic conditions and then to isolate the desired compounds of the general formula (I).

It is also possible to use, instead of said microorganisms, enzyme extracts and purified enzymes, if appropriate after addition or with regeneration of the required cofactors, which are obtainable by common methods starting from said microorganisms.

It is in particular also possible to clone genes determining the biosynthesis of such enzymes and express them in foreign hosts such as, for example, *Escherichia coli*. Recombinant bacteria of this type may be used immediately for biotransformation. In addition, it is also possible to use an enzyme extract of such a recombinant cell or a purified protein for biotransformation, where appropriate after addition or with regeneration of the required cofactors.

Preference is given to using for the method of the invention a microorganism from the group of actinomycetes, in particular of the genus *Streptomyces*.

Particular preference is given to using for the method of the invention a strain of the genus *Streptomyces djakartensis, Streptomyces griseofuscus, Streptomyces caelestis, Streptomyces antibioticus, Streptomyces griseus* or *Streptomyces aureofaciens*.

Very particular preference is given to using for the method of the invention a strain having the characteristic features of the following strains:

| Name | Deposition No. |
|---|---|
| *Streptomyces djakartensis* | NRRL B-12103 |
| *Streptomyces griseofuscus* | DSM 40191 |
| *Streptomyces caelestis* | DSM 40084 |
| *Streptomyces antibioticus* | ATCC 11891 |
| *Streptomyces griseus* | DSM 40937 |
| *Streptomyces aureofaciens* | DSM 46447 |

The strains mentioned in the table have been deposited again with the Deutsche Sammlung von Mikroorganismen und Zellkulturen GmbH (DSMZ), Mascheroder Weg 1b, D-38124 Brunswick, Germany, in accordance with requirements of the Budapest treaty:

| Name | Deposition No. |
|---|---|
| *Streptomyces djakartensis* | DSM 14327 |
| *Streptomyces griseofuscus* | DSM 14330 |
| *Streptomyces caelestis* | DSM 14328 |
| *Streptomyces antibioticus* | DSM 14329 |
| *Streptomyces griseus* | DSM 14331 |
| *Streptomyces aureofaciens* | DSM 14332 |

The strains are described in more detail in Example 16. It is possible to use not only the deposited strains per se but also mutants thereof, as long as these mutants have the characteristic features of the deposited strains, i.e. the mutants must still be capable of carrying out the bioconversion of the invention.

The aqueous nutrient medium preferably contains an assimilable carbon source and an assimilable nitrogen source.

The compounds of the formula (I) are produced, for example, when fermenting a strain of the species *Streptomyces djakartensis, S. gtiseofuscus, S. caelestis, S. antibioticus, S. griseus* or *S. aureofaciens* in an aqueous nutrient medium under aerobic conditions in the presence of compounds of the formula (II). The microorganisms are typically fermented in a nutrient medium containing a carbon source and, where appropriate, proteinaceous material. Preferred carbon sources include glucose, brown sugar, sucrose, glycerol, starch, corn starch, lactose, dextrin, molasses, etc. Preferred nitrogen sources include cotton seed meal, yeast, autolyzed bakers' yeast, solid milk constituents, soybean meal, cornmeal, pancreatic or papainic casein hydrolyzates, solid distillation components, broths of animal peptone, meat and bone fragments, etc. Preference is given to using combinations of these carbon and nitrogen sources. Trace elements such as, for example, zinc, magnesium, manganese, cobalt, iron, etc. need not be added to the culturing medium as long as tapwater and nonpurified constituents are being used as components of the medium.

Production of the compounds of the general formula (I) may be induced at any temperature which ensures sufficient growth of the microorganisms. The temperature is preferably between 21° C. and 32° C., particularly preferably approximately 28° C. Optimal production of the compounds of the formula (I) is usually achieved within 2 to 4 days after addition of the compounds of the formula (II) to the culture. The compounds of the invention may be produced both in shaker bottles and in stirred fermenters.

Preferred growth conditions and media for growing in shaker flasks are described in Examples 2 to 9.

The compounds of the invention as biotransformation product may be isolated from the culturing medium by common methods.

Various methods may be applied in order to isolate and purify the compounds of the invention from the fermentation broth, such as, for example, preparative gel chromatography, preparative chromatography on reversed phase or preparative absorption chromatography. The detection may be carried out, for example, by UV absorption or mass spectrometry.

The compounds of the invention may be used for preparing biologically active, in particular insecticidal and acaricidal, spinosyns. The biological efficacy of particular natural aglycone derivatives of spinosyn, which have a hydroxyl group in the C-8 position of the macrolide backbone, has recently been described (cf. WO 01/19840). Further examples which may be mentioned are spinosyn derivatives with a 3-hydroxy-1-butenyl radical in the C-21 position, which have likewise been described recently. Where appropriate, these spinosyn derivatives may also additionally carry a hydroxyl group in any of the abovementioned C-8 position and likewise have an insecticidal activity (cf. WO 01/19840).

It is advantageous to use suitable protective groups (PG) when preparing further spinosyn derivatives from the inventive compounds of the general formula (I) in which $R^1$ is hydrogen and D is the group C═O or C—O—$R^2$ where $R^2$ is hydrogen. Known examples of protective groups (PG) for hydroxyl groups are substituted methyl ethers and ethers, substituted ethyl ethers, substituted benzyl ethers, silyl ethers, esters, carbonates or sulfonates (cf. Greene T. W., Wuts P. G. W. in Protective Groups in Organic Synthesis; John Wiley & Sohns, Inc. 1999, Protection for the hydroxyl group, including 1,2- and 1,3-diols).

Examples of protective groups (PG) of the substituted methyl ether type, which may be mentioned, are: methoxymethyl (MOM) ethers, methylthiomethyl (MTM) ethers, (phenyl-dimethylsilyl)methoxymethyl (SMOM-OR) ethers, benzyloxymethyl (BOM-OR) ethers, para-methoxybenzyloxymethyl (PMBM-OR) ethers, para-nitrobenzyloxy-methyl ethers, ortho-nitrobenzyloxymethyl (NBOM-OR) ethers, (4-methoxyphenoxy)-methyl (p-AOM-OR) ethers, guaiacolmethyl (GUM-OR) ethers, tert-butoxymethyl ethers, 4-pentenyl-oxymethyl (POM-OR) ethers, silyloxymethyl ethers, 2-methoxyethoxy-methyl (MEM-OR) ethers, 2,2,2-trichloroethoxymethyl ethers, bis(2-chloroethoxy)-methyl ethers, 2-(trimethylsilyl)ethoxymethyl (SEM-OR) ethers, methoxy-methyl (MM-OR) ethers.

Examples of protective groups (PG) of the substituted ethyl ether type, which may be mentioned, are: 1-ethoxyethyl (EE-OR) ethers, 1-(2-chloroethoxy)ethyl (Cee-OR) ethers, 1-[2-(trimethylsilyl)ethoxy]ethyl (SEE-OR) ethers, 1-methyl-1-methoxyethyl (MIP-OR) ethers, 1-methyl-1-benzyloxyethyl (MBE-OR) ethers, 1-methyl-benzyloxy-2-fluoro-ethyl ethers, 1-methyl-1-phenoxy-ethyl ethers, 2,2,2-trichloroethyl ethers, 1,1-dianisyl-2,2,2-trichloroethyl (DATE-OR) ethers, 1,1,1,3,3,3-hexafluoro-2-phenyliso-propyl (HIP-OR) ethers, 2-trimethylsilylethyl ethers, 2-(benzylthio)ethyl ethers, 2-(phenyl-selenyl)ethyl ethers. Further examples of protective groups (PG) of the ether type, which may be mentioned, are: tetrahydropyranyl (THP-OR) ethers, 3-bromo-tetrahydropyranyl (3-BrTHP-OR) ethers, tetrahydrothiopyranyl ethers, 1-methoxy-cyclohexyl ethers, 2- and 4-picolyl ethers, 3-methyl-2-picolyl-N-oxido ethers, 2-quinolinylmethyl (Qm-OR) ethers, 1-pyrenylmethyl ethers, dipenylmethyl (DPM-OR) ethers, para,para'-dinitrobenzhydryl (RO-DNB) ethers, 5-dibenzosuberyl ethers, triphenylmethyl (Tr-OR) ethers, α-naphthyldiphenyhnethyl ethers, para-methoxy-phenyldiphenylmethyl (MMTr-OR) ethers, di(para-methoxy-phenyl)phenylmethyl (DMTr-OR) ethers, tri(para-methoxy-phenyl)methyl (TMTr-OR) ethers, 4-(4'-bromo-phenacyloxy)phenyldiphenylmethyl ethers, 4,4',4"-tris(4,5-dichlorophthalimido-phenyl)methyl (CPTr-OR) ethers, 4,4',4"-tris(levulinoyloxy-phenyl)methyl (TLTr-OR) ethers, 4,4',4"-tris(benzoyloxyphenyl)-methyl (TBTr-OR) ethers, 4,4'-dimethoxy-3"-[N-(imidazolylmethyl)]-trityl (IDTr-OR) ethers, 4,4'-dimethoxy-3"-[N-(imidazolylethyl)carbamoyl]trityl (IETr-OR) ethers, 1,1-bis(4-methoxy-phenyl)-1' -pyrenylmethyl (Bmpm-OR) ethers, 9-anthryl ethers, 9-(9-phenyl)xanthenyl (pixyl-OR) ethers, 9-(9-phenyl-10-oxo)anthryl (tritylon ethers). 4-Methoxy-tetrahydropyranyl (MTHP-OR) ethers, 4-methoxy-tetrahydrothio-pyranyl ethers, 4-methoxy-tetrahydrothio-pyranyl ether S,S-dioxide, 1-[(2-chloro-4-methyl)phenyl]-4-methoxypiperidin-4-yl (CTMP-OR) ethers, 1-(2-fluorophenyl)-4-methoxy-piperidin-4-yl (Fpmp-OR) ethers, 1,4-dioxan-2-yl ethers, tetrahydrofuranyl ethers, tetrahydrothiofuranyl ethers, 2,3,3a,4,5,6,7,7a-octahydro-7,8,8-trimethyl-4,7-methanebenzofuran-2-yl (RO-MBF) ethers, tert-butyl ethers, allyl ethers, propargyl ethers, para-chlorophenyl ethers, para-methoxyphenyl ethers, para-nitrophenyl ethers, 2,4-dinitro-phenyl (RO-DNP) ethers, 2,3,5,6-tetrafluoro-4-(trifluoromethyl)phenyl ethers, benzyl (Bn-OR) ethers. Examples of protective groups of the substituted benzyl ether type, which may be mentioned, are: para-methoxybenzyl (MPM-OR) ethers, 3,4-dimethoxy-benzyl (DMPM-OR) ethers, ortho-nitrobenzyl ethers, para-nitrobenzyl ethers, para-halobenzyl ethers, 2,6-dichloro-benzyl ethers, para-cyanobenzyl ethers, para-phenyl-benzyl ethers, 2,6-difluorobenzyl ethers, para-aminoacylbenzyl. (PAB-OR) ethers, para-azidobenzyl (Azb-OR) ethers, 4-azido-3-chlorobenzyl ethers, 2-trifluoromethyl-benzyl ethers, para-(methylsulfinyl)benzyl (Msib-OR) ethers. Examples of protective groups (PG) of the silyl ether type, which may be mentioned are: trimethylsilyl (TMS-OR) ethers, triethylsilyl (TES-OR) ethers, triiso-propylsilyl (TIPS-OR) ethers, dinethylisopropyl-silyl (IPDMS-OR) ethers, diethylisopropylsilyl (DEIPS-OR) ethers, dimethylhexylsilyl (TDS-OR) ethers, tert-butyldimethylsilyl (TBDMS-OR) ethers, tert-butyldiphenylsilyl (TBDPS-OR) ethers, tribenzylsilyl ethers, tri-para-xylylsilyl ethers, triphenylsilyl (TPS-OR) ethers, diphenylmethylsilyl (DPMS-OR) ethers, di-tert-butylmethylsilyl (DTBMS-OR) ethers, tris(trimethylsilyl)silyl ethers (sisyl ether), (2-hydroxystyryl)-dimethylsilyl (HSDMS-OR) ethers, (2-hydroxystyryl)diisopropylsilyl (HSDIS-OR) ethers, tert-butylmethoxyphenylsilyl (TBMPS-OR) ethers, tert-butoxydiphenylsilyl (DPTBOS-OR) ethers. Examples of protective groups (PG) of the-ester type, which may be mentioned, are: formic esters, benzoylformic esters, acetic esters (RO-Ac), chloroacetic esters, dichloroacetic esters, trichloroacetic esters, trifluoroacetic esters (RO-TFA), methoxy-acetic esters, triphenylmethoxyacetic esters, phenoxyacetic esters, para-chlorophenoxy-acetic esters, phenylacetic esters, diphenylacetic esters (DPA-OR), nicotinic esters, 3-phenylpropionic esters, 4-pentenoic esters, 4-oxopentanoic esters (levulinates) (Lev-OR), 4,4-(ethylenedithio)-pentanoic esters (RO-LevS), 5-[3-bis(4-methoxyphenyl)hydroxy-methylphenoxy]-levulinic esters, pivalic esters (Pv-OR), 1-adamantanecarboxylic esters, crotonic esters, 4-methoxy-crotonic esters, benzoic esters (Bz-OR), para-phenyl-benzoic esters, 2,4,6-trimethylbenzoic esters (mesitoic esters), 4-(methylthiomethoxy)-butyric esters (MTMB-OR), 2-(methylthiomethoxymethyl)benzoic esters (MTMT-OR). Examples of protective groups (PG) of the ester type, which may be mentioned, are: methyl carbonate, methoxymethyl carbonate, 9-fluorenylmethyl carbonate (Fmoc-OR), ethyl carbonate, 2,2,2-trichloroethyl carbonate (Troc-OR), 1,1-dimethyl-2,2,2-trichloroethyl carbonate (TCBOC-OR), 2-(trimethylsilyl)ethyl carbonate (TMSEC-OR), 2-(phenylsulfonyl)-ethyl carbonates (Psec-OR), 2-(triphenylphosphonio)-ethyl carbonates (Peoc-OR), tert-butyl carbonate (Boc-OR), isobutyl carbonate, vinyl carbonate, allyl carbonate (Alloc-OR), p-nitrophenyl carbonate, benzyl carbonate (Z-OR), para-methoxybenzyl carbonate, 3,4-dimethoxybenzyl carbonate, ortho-nitrobenzyl carbonate, para-nitrobenzyl carbonate, 2-dansylethyl carbonate (Dnseoc-OR), 2-(4-nitrophenyl)-ethyl carbonate (Npeoc-OR), 2-(2,4-dinitrophenyl)ethyl carbonate (Dnpeoc-OR). Examples of protective groups (PG) of the sulfonate type, which may be mentioned, are: allylsulfonate (Als-OR), methanesulfonates (Ms-OR), benzylsulfonates, tosylates (Ts-OR), 2-[(4-nitrophenyl)ethyl]sulfonates (Npes-OR).

When preparing further spinosyn derivatives from the abovementioned compounds of the general formula (I), it may be quite advantageous to block initially the 1-hydroxyethyl radical in the C-21 position and, where appropriate, the hydroxyl group in the C-9 position (where $R^2$=H) with suitable, for example one of the abovementioned, protective groups (PG). The use of two different protective groups ($PG^1$ and $PG^2$, respectively) is recommended here, and these protective groups should be appropriately compatible, i.e. removable from one another selectively and independently. Subsequently, a derivatization, for example glycosidation, by means of chemical synthesis or by microbial bioconversion (cf. also U.S. Pat. No. 5,539,089; introduction of the radicals R or R') may take place on the hydroxyl group in the C-17 position to give the spinosyn derivatives (Ia-2 or Ib-2) (cf. schemes 2 and 3).

Scheme 2 - Protective group strategy

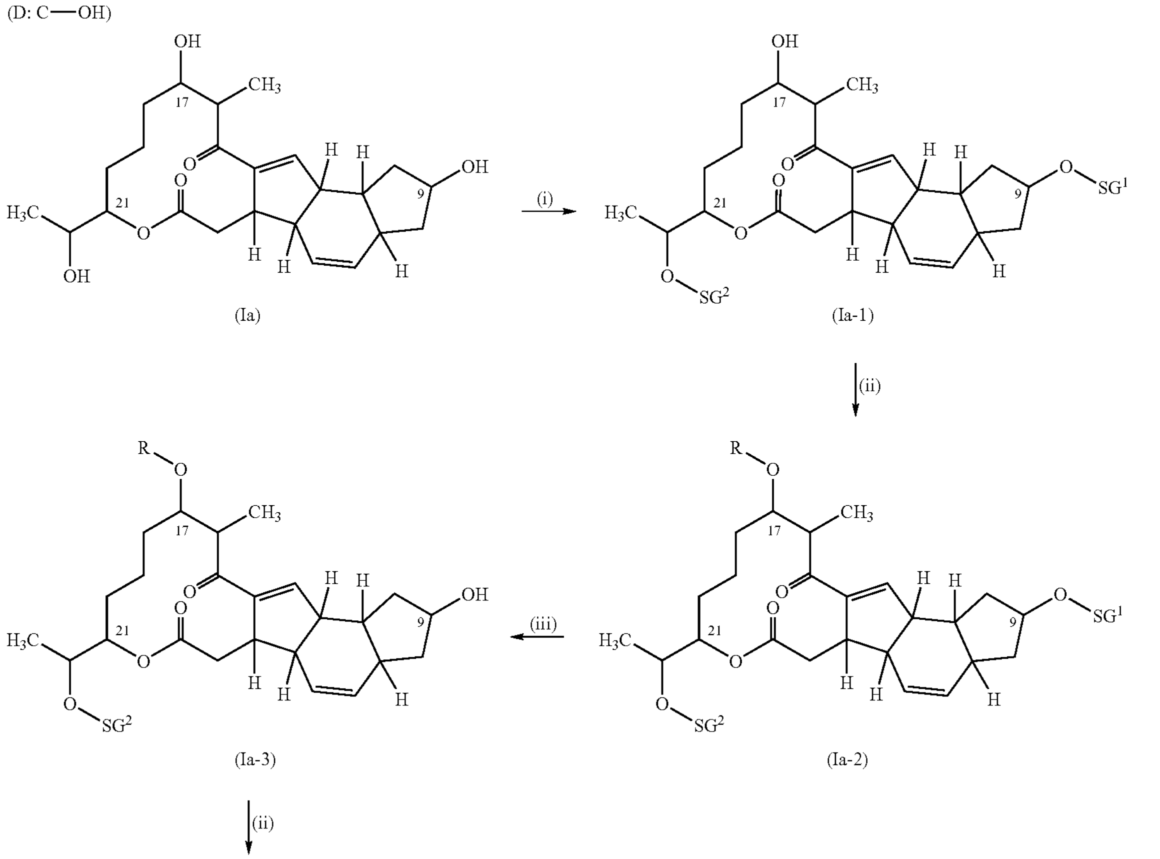

(Ia) (Ia-1) (Ia-2) (Ia-3)

-continued
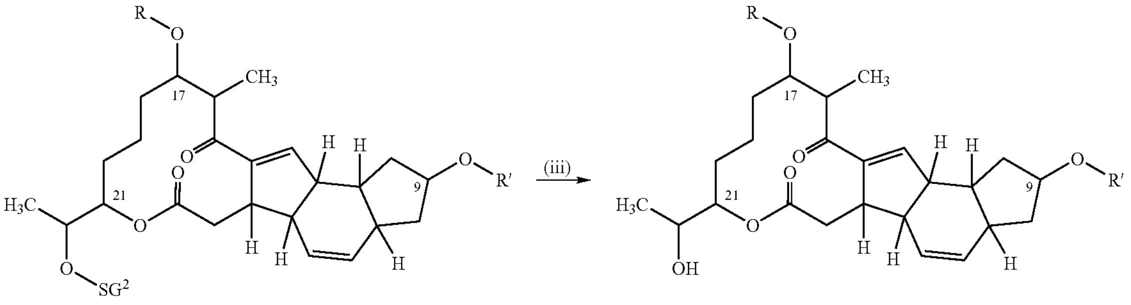
(Ia-4) (Ia-5)
(i) Introduction-protective group (PG[1], PG[2])
(ii) Derivatization-e.g. glycosidation (R and R′, respectively)
(iii) Deblocking-protective group (PG)/or selective deblocking-protective group (e.g. PG[1])
Scheme 3 - Protective group strategy
(D: C=O)
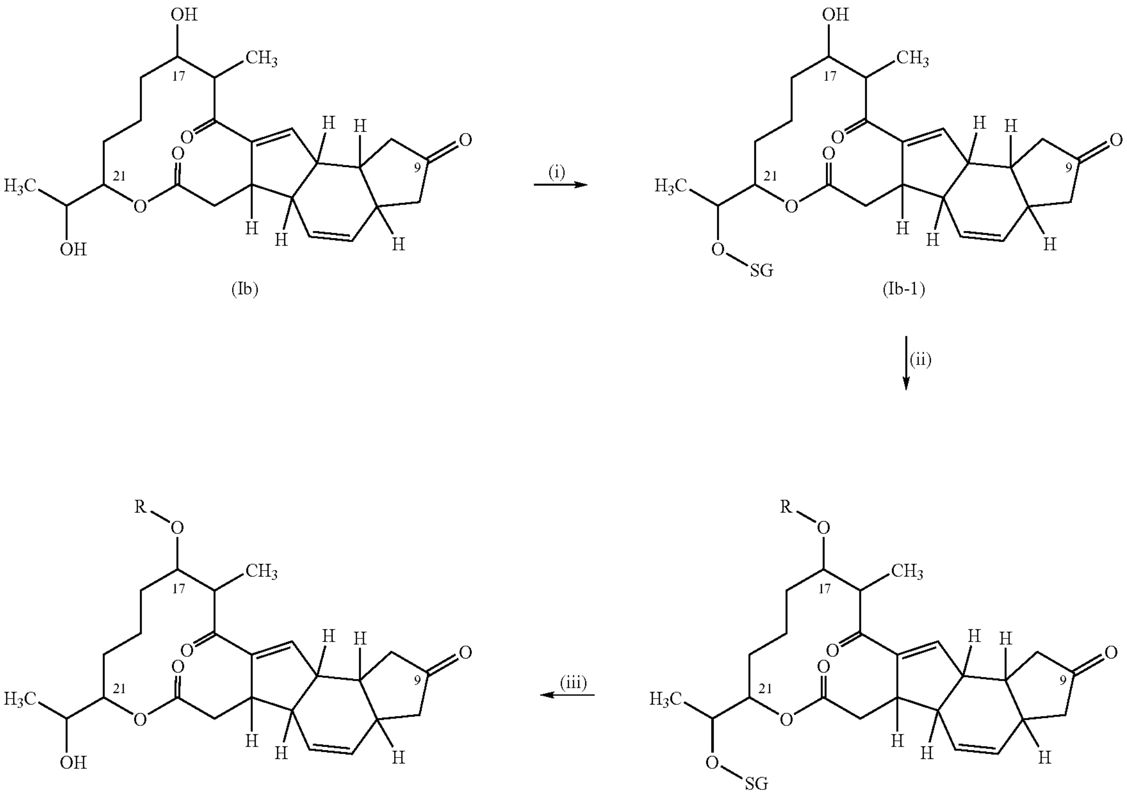
(Ib) (Ib-1)
(Ib-3) (Ib-2)
(i) Introduction-protective group (PG)
(ii) Derivatization-e.g. glycosidation (R)
(iii) Deblocking-protective group (PG)

After successful derivatization in positions. C-9 and, respectively, C-17 (cf Ia-4) or C-17 (cf. Ib-2), the remaining protective group (PG) can be removed and the spinosyn derivative of the general formula (I) be obtained.

EXAMPLES

Example 1

Strains Used

Table: Strains capable of biotransformation of the compound (IIa) to give the corresponding derivatives having a 1-hydroxy-ethyl radical in the C-21 position (compound (Ia)):

| Name | Internal reference | Deposition No. |
|---|---|---|
| *Streptomyces djakartensis* | NRRL B-12103 | DSM 14327 |
| *Streptomyces griseofuscus* | DSM 40191 | DSM 14330 |
| *Streptomyces caelestis* | DSM40084 | DSM 14328 |
| *Streptomyces antibioticus* | ATCC 11891 | DSM 14329 |
| *Streptomyces griseus* | DSM 40937 | DSM 14331 |
| *Streptomyces aureofaciens* | DSM 46447 | DSM 14332 |

ATCC = American Type Culture Collection, Manassas, VA, U.S.A.
DSM = Deutsche Sammlung für Mikroorganismen und Zellkulturen, Brunswick, Germany.
NRRL = Agricultural Research Service Culture Collection, Peoria, IL, U.S.A.

Example 2

Biotransformation Using *S. djakartensis* NRRL B-12103

Exemplary biotransformation protocol for producing the compound (Ia) from the compound (IIa).

The producer cultures were prepared by inoculating 20 ml of R5A medium (per liter of R5A medium: 103 g of sucrose; 0.25 g of $K_2SO_4$; 10.12 g of $MgCl_2$; 10 g of glucose; 5 g of yeast extract; 0.1 g of casamino acids, 21 g of MOPS buffer pH 6:8 (KOH), 2 ml of trace element solution; trace element solution: (per liter) 40 mg of $ZnCl_2$, 200 mg of $FeCl_3 \times 6\ H_2O$, 10 mg of $CuCl_2 \times 2H_2O$, 10 mg of $MnCl_2 \times 4\ H_2O$, 10 mg of $Na_2B_4O_7 \times 10\ H_2O$, 10 mg of $(NH_4)_6Mo_7O_{24} \times 4\ H_2O$; (Fernandez et al., 1998, J. Bacteriol. 180: 4929; Hopwood et al., 1985, Genetic manipulation of *Streptomyces*. A laboratory manual. The John Innes Foundation, Norwich, England) in 100 ml Erlenmeyer flasks with in each case 50 µl of *S. djakartensis* NRRL B-12103 spore suspension. Prior to inoculation, the medium was sterilized at 121° C. and an overpressure of 1.1 for 20 minutes. The cultures were incubated at 28° C. and 200 rpm. After 24 hours and after 72 hours of incubation, in each case 1 mg of the compound (IIa) (100 µl of a stock solution of 10 mg/ml in methanol) was added. The biotransformation was stopped after 120 hours. The cultures were removed by centrifugation (4000 rpm, 10 minutes) and the supernatant was admixed with the same volume of methanol.

Example 3

Biotransformations Using *Streptomyces griseofuscus*

Exemplary biotransformation protocol for producing the compound (Ia) from the compound (IIa).

The producer cultures were prepared by applying the method of Example 2, using 50 µl of spore suspension of the strain *Streptomyces griseofuscus* instead of the strain *S. djakartensis* NRRL B-12103.

Example 4

Biotransformations Using *Streptomyces caelestis*

Exemplary biotransformation protocol for producing the compound (Ia) from the compound (IIa).

The producer cultures were prepared by applying the method of Example 2, using 50 µl of spore suspension of the strain *Streptomyces caelestis* instead of the strain *S. djakartensis* NRRL B-12103.

Example 5

Biotransformations Using *Streptomyces antibioticus*

Exemplary biotransformation protocol for producing the compound (Ia) from the compound (IIa).

The producer cultures were prepared by applying the method of Example 2, using 50 µl of spore suspension of the strain *Streptomyces antibioticus* instead of the strain *S. djakartensis* NRRLB-12103.

Example 6

Biotransformations Using *Streptomyces griseus*

Exemplary biotransformation protocol for producing the compound (Ia) from the compound (IIa).

The producer cultures were prepared by applying the method of Example 2, using 50 µl of spore suspension of the strain *Streptomyces griseus* instead of the strain *S. djakartensis* NRRL B-12103.

Example 7

Biotransformations Using *Streptomyces aureofaciens*

Exemplary biotransformation protocol for producing the compound (Ia) from the compound (IIa).

The producer cultures were prepared by applying the method of Example 2, using 50 µl of spore suspension of the strain *Streptomyces aureofaciens* instead of the strain *S. djakartensis* NRRL B-12103.

Example 8

Biotransformations Using *Streptomyces djakartensis*

Exemplary biotransformation protocol for producing spinosyn A with a 1-hydroxy-ethyl radical in the C-21 position [compound of the general formula (I) in which $R^1$ is an amino sugar of the formula 1a, A-B is the group —HC═CH— and D is the group —CO—$R^2$ where $R^2$ is a sugar of the formula 2a].

The producer cultures were prepared by inoculating 20 ml of R5A medium (R5A medium: see Example 2) in 100 ml Erlenmeyer flasks with in each case 50 µl of *S. djakartensis* NRRL B-12103 spore suspension. Prior to inoculation, the medium was sterilized at 121° C. and an overpressure of 1.1 bar for 20 minutes. The cultures were incubated at 28° C. and 200 rpm. After 48 hours of incubation, 2 mg of spinosyn A (100 µl of a stock solution, of 10 mg/ml in methanol) were added. The biotransformation was stopped after 96 hours. The cultures were removed by centrifugation (4000 rpm, 10 minutes) and the supernatant was admixed with the same volume of methanol.

Example 9

Biotransformations Using *Streptomyces djakartensis*

Exemplary biotransformation protocol for producing 17-pseudo-spinosyn aglycone A with a 1-hydroxy-ethyl radical in the C-21 position [compound of the general formula (I) in which $R^1$ is hydrogen, A-B is the group —HC═CH— or —HC═C($CH_3$)— and D is the group —CO—$R^2$ where $R^2$ is a sugar of the formula 2a].

The producer cultures were prepared by inoculating 20 ml of R5A medium (R5A medium: see Example 2) in 100 ml Erlenmeyer flasks with in each case 50 A1 of *S. djakartensis* NRRL B-12103 spore suspension. Prior to inoculation, the medium was, sterilized at 121° C. and an overpressure of 1.1 bar for 20 minutes. The cultures were incubated at 28° C. and 200 rpm. After 48 hours of incubation, 2 mg of 17-pseudo-spinosyn aglycone A or D (100 µl of a stock solution of 10 mg/ml in methanol) were added. The biotransformation was stopped after 96 hours. The cultures were removed by centrifugation (4000 rpm, 10 minutes) and the supernatant was admixed with the same volume of methanol.

Example 10

Isolation of the Compound (Ia) from the Biotransformation with *S. djakartensis* NRRL B-12103

Exemplary protocol for working up the culture supernatants and concentrating the compound (Ia).

35 ml of the culture supernatant of Example 2, to which methanol had been added, were reduced to about 20 ml and admixed with 10 ml of water. This was followed by extracting twice with in each case 10 ml of ethyl acetate, concentrating the combined organic phases to dryness and resuspending the residue in 400 µl of methanol. An aliquot of this solution was analyzed via HPLC/MS (Example 11).

Example 11

Analytical HPLC/UV/MS

Exemplary protocol for analyzing the worked-up culture supernatants by means of HPLC/UV/MS.

An aliquot of the worked-up culture, supernatant of the biotransformation with *S. djakartensis* (Example 2) were subjected to chromatography on a reversed-phase HPLC column (2.1×250 mm) with a gradient of water to which ammonium acetate (25 mmol/l) had been added and methanol to which ammonium acetate (25 mmol/l) had been added and a flow rate of 250 p/minute. The detection is carried out using UV (245 nm) and electrospray (positive) mass spectrometry on a quadrupole mass spectrometer.

Compound (Ia) has a molecular weight of 418 Dalton and is detected as $[M+NH_4]^+$ ion at m/z=436 under these conditions. The retention time of approx. 32.5 minutes is shorter than that of the compound (IIa), which is approx. 37.5 minutes.

Example 12

Extraction and Preparative Preparation in Pure Form of the Compound (Ia) from Shaker Cultures of the Biotransformation with *S. djakartensis* NRRL B-12103

Fifteen 20 ml cultures of the strain (*S. djakartensis*) were grown in 100 ml Erlenmeyer flasks according to the method described in Example 2 and the culture supernatants were combined to work up compound (Ia). The combined culture supernatants were worked up as described in Example 11. The residue was resuspended in about 3 ml of methanol. The compound (Ia) was isolated via chromatography on an analytical reversed-phase HPLC column (4.6×250 mm) with a gradient of 25 mmol/l ammonium acetate in water and 25 mmol/l ammonium acetate in methanol. An aliquot of 100 µl was injected for each run. The UV-detection was carried out at 245 nm. The fractions were collected manually, combined and evaporated to dryness. The yield was approximately 1 mg.

Example 13

Elucidation of the Structure of the Compound (Ia)

The preparatively isolated compound (Ia) was resuspended in $CD_3OD$ and studied by nuclear magnetic resonance (NMR). $^1H$-NMR, COSY, TOCSY, HSQC and HMBC spectra were recorded. The table below summarizes the results.

NMR data of compound (Ia) in $CD_3OD$ (500 MHz)

| Position | $\delta_C$ [ppm] | $\delta_H$ [ppm] | Mult. | J [Hz] | Int. |
|---|---|---|---|---|---|
| 1 | 174 | — | | — | — |
| 2 | 35 | 2.48 | dd | 14/3 | 1H |
| | | 3.12 | dd | 14/5 | 1H |
| 3 | 49 | 2.93 | ddd | 10/5/2 | 1H |
| 4 | 43 | 3.49 | m | | 1H |
| 5 | 129 | 5.84 | ddd | 10/3/3 | 1H |
| 6 | 131 | 5.91 | d br. | 10 | 1H |
| 7 | 42 | 2.23 | m | | 1H |
| 8 | 41 | 1.46 | m | | 1H |
| | | 1.83 | dd | 13/7 | 1H |
| 9 | 73 | 4.34 | m | | 1H |
| 10 | 40 | 1.24 | m | | 1H |
| | | 2.34 | m | | 1H |
| 11 | 47 | 0.94 | m | | 1H |
| 12 | 51 | 2.85 | m | | 1H |
| 13 | 150 | 7.00 | s br. | | 1H |
| 14 | 146 | — | | | — |
| 15 | 206 | — | | | — |
| 16 | 50 | 3.22 | m | | 1H |
| 17 | 73 | 3.49 | m | | 1H |
| 18 | 36 | 1.43 | m | | 1H |
| | | 1.48 | m | | 1H |
| 19 | 23 | 1.28 | m | | 1H |
| | | 1.71 | m | | 1H |
| 20 | 27 | 1.48 | m | | 1H |
| | | 1.63 | m | | 1H |
| 21 | 79 | 4.70 | ddd | 10/5/2 | 1H |
| 22 | 70 | 3.65 | m | | 1H |
| 23 | 18 | 1.04 | d | 7 | 3H |
| 24 | 16 | 1.15 | d | 7 | 3H |

(Ia)

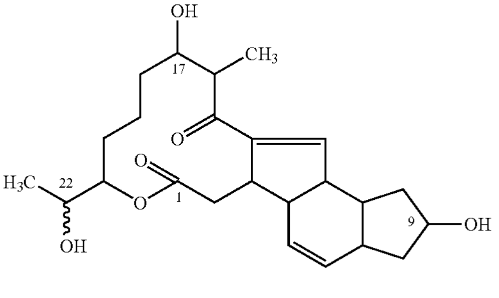

Examples 14

Analytical Detection of the Hydroxylated Spinosyn A Produced 20 ml of the culture supernatant of the biotransformation of Example 8 to which methanol had been added, were adjusted to pH 5 with a 0.01 N NaOH solution and concentrated to approx. 5 ml of aqueous residue which was then extracted twice with in each case 5 ml of ethyl acetate. The combined organic phases were concentrated to dryness in an $N_2$ stream and resuspended in 200 µl of methanol. An aliquot of this extract was studied by means of LC/MS and LC/MS/MS on a tandem mass spectrometer with electrospray positive ionization.

In the LC/MS chromatogram of the extract a peak appears at 40.0 minutes with $[M+H]^+$ m/z=748.5 at low concentration. The spectrum of the daughter ions of this ion has a fragment with m/z=142 which is characteristic for the removal of a forosamine unit.

Examples 15

Analytical Detection of the Hydroxylated 17-pseudo-spinosyn Aglycone Produced 20 ml of the culture supernatant of the biotransformation of Example 9 to which methanol had been added, were adjusted to pH 5 with a 0.01 N NaOH solution and concentrated to approx. 5 ml of aqueous residue which was then extracted twice with in each case 5 ml of ethyl acetate. The combined organic phases were concentrated to dryness in an $N_2$ stream and resuspended in 200 µl of methanol. An aliquot of this extract was studied by means of LC/MS and LC/MS/MS on a tandem mass spectrometer with electrospray positive ionization.

In the LC/MS chromatogram of the extract a peak appears at 38.8 minutes with $[M+NH_4]^+$ m/z=624.4 at low concentration. This corresponds to a hydroxylated product of 17-pseudo-spinosyn A aglycone. The spectrum of the daughter ions of this ion has a fragment with m/z=189 which is characteristic for the removal of a trimethylrhamnose unit.

Example 16

Characterization of the Strains Used a) *Streptomyces djakartensis* NRRL B-12103:

This strain was obtained as a niddamycin producer from the Agricultural Research Service Culture Collection (1815 N. University Street, Illinois 61604, U.S.A.) with accession number NRRL B-12103. The strain is described in U.S. Pat. No. 3,646,194. The culture was deposited again with the Deutsche Sammlung von Mikroorganismen und Zellkulturen GmbH (DSMZ), Mascheroder Weg 1b, D-38124 Brunswick, Germany with deposition number DSM 14327 in accordance with the requirements of the Budapest treaty on 06.06.2001.

b) *Streptomyces griseofuscus* DSM 40191:

This strain was obtained as bundlin A, B, moldicidin A and pentarnycin producer from the Deutsche Sammlung von Mikroorganismen und Zellkulturen (Mascheroder Weg 1b, D-38124 Brunswick, Germany) with accession number 40191. The culture was deposited again with the Deutsche Sammlung von Mikroorganismen und Zellkulturen GmbH (DSMZ), Mascheroder Weg 1b, D-38124 Brunswick, Germany, with deposition number, DSM 14330 in accordance with the requirements of the Budapest treaty on 06.06.2001.

c) *Streptomyces caelestis* DSM 40084:

This strain was obtained as caelesticetin producer from the Deutsche Sammlung von Mikroorganismen und Zellkulturen (Mascheroder Weg 1b, D-38124 Brunswick, Germany) with accession number 40084. The culture was deposited again with the Deutsche Sammlung von Mikroorganismen und Zellkulturen GmbH (DSMZ), Mascheroder Weg 1b, D-38124 Brunswick, Germany, with deposition number DSM 14328 in accordance with the requirements of the Budapest treaty on 06.06.2001.

d) *Streptomyces antibioticus* ATCC 11891:

This strain was obtained as a caelesticetin producer from the American Type Culture Collection (10801 University Boulevard, Manassas, Va. 20110-2209, USA) with accession number ATCC 11891. The culture was deposited again with the Deutsche Sammlung von Mikroorganismen und Zellkulturen GmbH (DSMZ), Mascheroder Weg 1b, D-38124 Brunswick, Germany, with deposition number DSM 14329 in accordance with the requirements of the Budapest treaty on 06.06.2001.

e) *Streptomyces griseus* DSM 40937:

This strain was obtained from the Deutsche Sammlung von Mikroorganismen und Zellkulturen (Mascheroder Weg 1b, D-38124 Brunswick, Germany) with accession number 40937. The culture was deposited again with the Deutsche Sammlung von Mikroorganismen und Zellkulturen GmbH (DSMZ), Mascheroder Weg 1b, D-38124 Brunswick, Germany, with deposition number DSM 14331 in accordance with the requirements of the Budapest treaty on 06.06.2001.

f) *Streptomyces aureofaciens* DSM 46447:

This strain was obtained as tetracycline producer from the Deutsche Sammlung von Mikroorganismen und Zellkulturen (Mascheroder Weg 1b, D-38124 Brunswick, Germany) with accession number 40084. The culture was deposited again with the Deutsche Sammlung von Mikroorganismen und Zellkulturen GmbH (DSMZ), Mascheroder Weg 1b, D-38124 Brunswick, Germany, with deposition number DSM 14332 in accordance with the requirements of the Budapest treaty on 06.06.2001.

Example 17

Preparation of the Starting Compounds

Spinosyn A Aglycone (IIa)

The spinosyn A aglycone (IIa) [compound of the general formula (II) in which $R^1$ is hydrogen, A-B is the group —HC=CH— and D is the group C—OH] was prepared from Tracer® as described in WO 01/16303.

9-Keto-spinosyn A Aglycone (IIb)

The 9-keto-spinosyn A aglycone (IIb) [compound of the general formula (II) in which $R^1$ is hydrogen, A-B is the group —HC=CH— and D is the group C=O] was prepared from the compound (IIa) by means of pyridinium dichromate oxidation:

46.55 g (115.6 mmol) of the spinosyn A aglycone (IIa) were dissolved in 1100 ml of abs. dichloromethane under inert gas and admixed with 43.51 g (115.6 mmol) of pyridinium dichromate. After stirring at 25° C. for 4 hours and addition of 900 ml of diethyl ether, the precipitated chromium salts were filtered off and the filtrate was concentrated under reduced pressure. Column chromatography on silica gel (eluent: cyclohexane/ethyl acetate 1:1, followed by 100% ethyl acetate) delivered 3.68 g of 9,17-diketospinosyn aglycone and 23.40 g of an approx. 9:1 mixture of the spinosyn A aglycone (IIa) and the 17-keto-spinosyn aglycone (IIb) in addition to 11.74 g of recovered spinosyn A aglycone (IIa). Recrystallization of the mixture in cyclohexane/ethyl acetate concentrates the 9-keto-spinosyn A aglycone (IIb) to >98%. 20.78 g of 9-keto-spinosyn A aglycone (IIb) are obtained in the form of colorless crystals.

TLC: $R_f$ ($SiO_2$, ethyl acetate=0.44—$^1$H-NMR: $CDCl_3$, δ=6.77 (s, 13-H); 5.97 (d, 6-H); 5.88 (m, 5-H); 4.72 (m, 21-H); 3.69 (m, 17-H) inter alia—LC/ESI-MS: m/z=401 (25%) $[M]^+$, 289 (100%).

Diketospinosyn aglycone: TLC: $R_f$ ($SiO_2$, ethyl acetate) =0.64—$^1$H-NMR: $CDCl_3$, δ=6.92 (s, 13-H); 5.97 (d, 6-H); 5.87 (m, 5-H); 4.85 (m, 21-H); 4.25 (q, 16-H) inter alia—LC/ESI-MS: m/z=399 (100%) $[M+H]^+$.

Spinosyn A

The preparation of spinosyn A was initially carried out as described in WO 01/16303. The spinosyn A/D mixture obtained was fractionated by chromatography on a preparative reversed-phase column (250×8 mm). The eluents used were water containing 25 mmol/l ammonium acetate (A) and methanol containing 25 mmol/l ammonium acetate (B). Elution was carried out using a gradient of from 60% B to 100% B in 35 minutes. The flow rate was 3 ml/minute. The separated substances were detected by a TV detector at 242 nm and automatically fractionated. Spinosyn A eluted at approx. 31 minutes and spinosyn D at approx. 33 minutes. The combined fractions of spinosyn A from several injections were evaporated down to the aqueous residue under reduced pressure in the rotary evaporator. Said aqueous solution was freeze-dried and spinosyn A was obtained as a white solid.

17-Pseudospinosyn A/D Aglycone

The 17-pseudospinosyn A/D aglycone was prepared as described in WO 01/16303.

The invention claimed is:

1. A compound of the formula (I), (I)

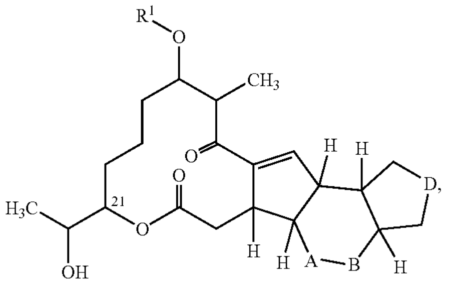

in which

A-B is any of the following groups: —HC═CH—, —HC═C($CH_3$)—, —$H_2$C—$CH_2$— or —$H_2$C—CH($CH_3$)—, D is the group

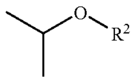

or

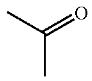

, $R^1$ is an amino sugar, and $R^2$ is a sugar, wherein in the case (1) that in the compound of the formula (I)

A-B is any of the following groups: —HC═CH—, —HC═C($CH_3$)—, —$H_2$C—$CH_2$— or —$H_2$C—CH($CH_3$)— and D is the group

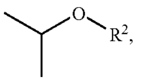

$R^1$ is an amino sugar of the formula 1a

1a

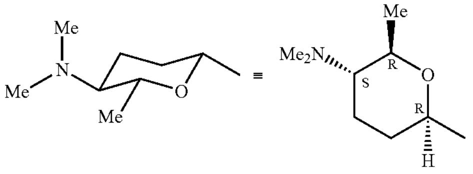

and $R^2$ is a sugar of the formula 2a

2a

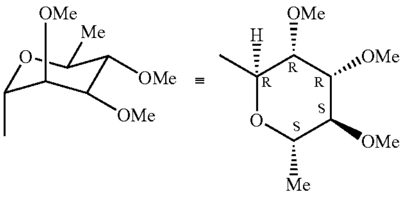

or, in the case (2) that in the compound of the formula (I)

A-B is the group —HC═CH— or —$H_2$C—$CH_2$— and

D is as defined above, $R^1$ is an amino sugar of the abovementioned formula 1a and $R^2$ is hydrogen or a sugar of the formula 2b, 2c, 2d, 2e or 2f 2b

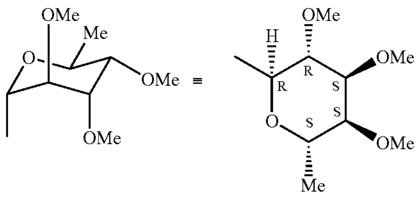

-continued

2c

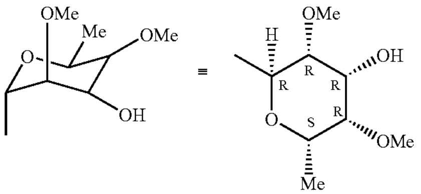

2d

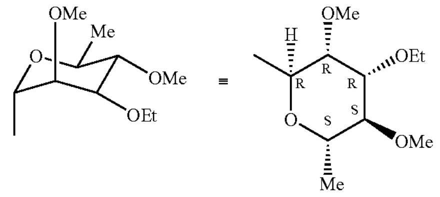

2e

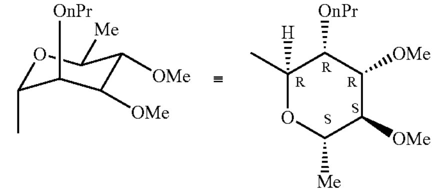

2f

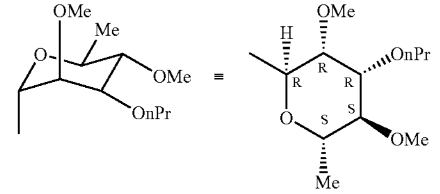

or, in the case (3) that in the compound of the formula (I)

A-B is one of the following groups: —HC═CH—, —HC═C($CH_3$)— or —$H_2C$—$CH_2$— and D is as defined above, $R^1$ is hydrogen or an amino sugar of the formula 1b 1b

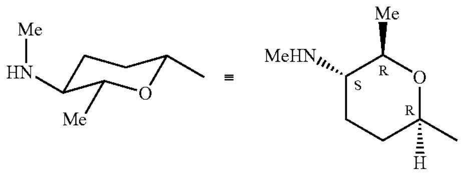

and $R^2$ is hydrogen or a sugar of the abovementioned formula 2a or, in the case (4) that in the compound of the formula (I)

A-B is the group —HC═CH— or —HC═C($CH_3$)— and

D is as defined above, $R^1$ is an amino sugar of the abovementioned formula 1a and $R^2$ is a sugar of the formula 2g, 2h, 2i, 2j or 2k 2g

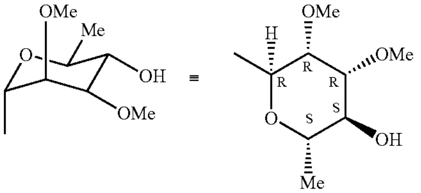

2h

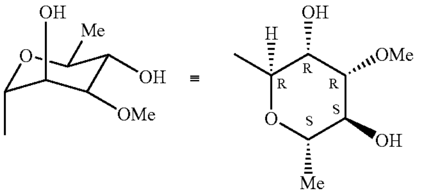

2i

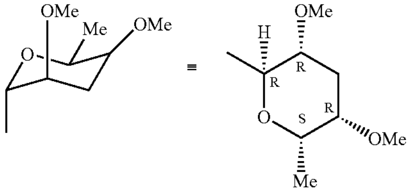

2j

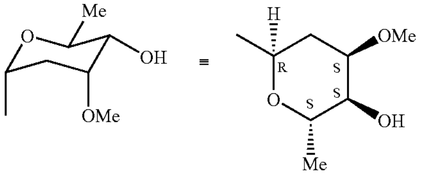

2k

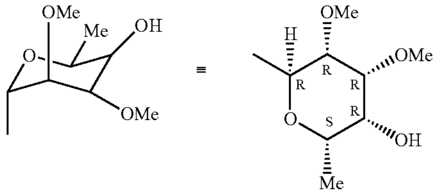

or, in the case (5) that in the compound of the formula (I)

A-B is the group —HC═CH— or —$H_2C$—$CH_2$— and

D is as defined above, $R^1$ is an amino sugar of the abovementioned formula 1a and $R^2$ is a sugar of the formula 2l or 2m 2l

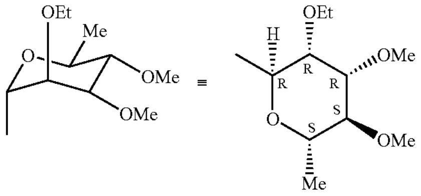

-continued

2m

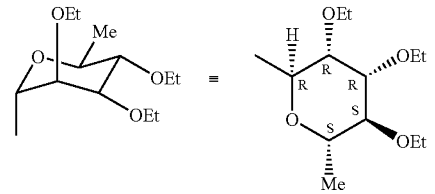

or, in the case (6) that in the compound of the formula (I)

A-B is the group —HC═CH— or —HC═C($CH_3$)— and

D is as defined above, $R^1$ is hydrogen or an amino sugar of the abovementioned formula 1b or an amino sugar of the formula 1c 1c

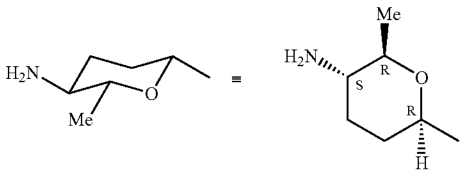

and $R^2$ is a sugar of the abovementioned formula 2b, 2c, 2g or 2h or a sugar of the formula 2n 2n

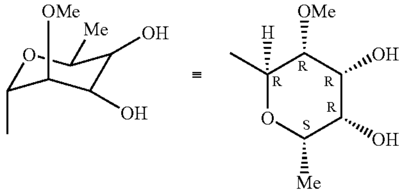

or, in the case (7) that in the compound of the formula (I)

A-B is the group —HC═CH— and

D is as defined above, $R^1$ is an amino sugar of the abovementioned formula 1a and $R^2$ is a sugar of the formula 2o 2o

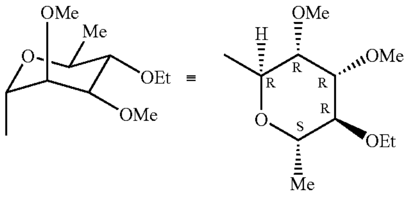

or, in the case (8) that in the compound of the formula (I)

A-B is the group —HC═CH— and

D is as defined above, $R^1$ is an amino sugar of the abovementioned formula 1b and $R^2$ is a sugar of the abovementioned formula 2d, 2i or 2j or a sugar of the formula 2p 2p

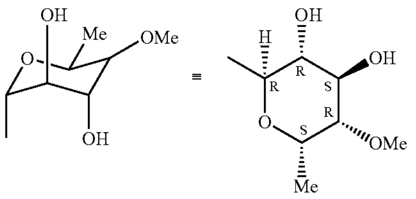

or, in the case (9) that in the compound of the formula (I)

A-B is the group —HC═CH— and

D is as defined above, $R^1$ is hydrogen or an amino sugar of the abovementioned formula 1c and $R^2$ is a sugar of the abovementioned formula 2i or 2p or, in the case (10) that in the compound of the formula (I)

A-B is the group —HC═CH— and

D is as defined above, $R^1$ is amino sugar of the abovementioned formula 1d, 1e or an amino sugar of the formula 1f 1d

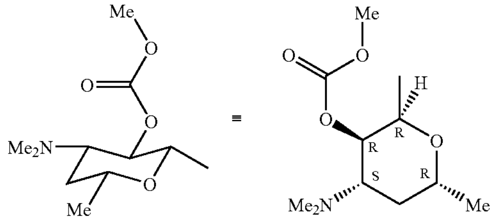

1e

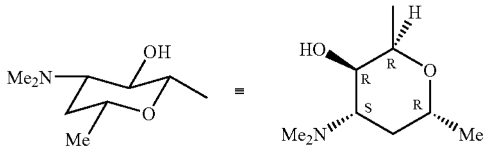

1f

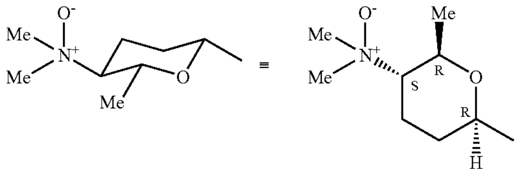

and $R^2$ is a sugar of the abovementioned formula 2a or, in the case (11) that in the compound of the formula (I)

A-B is the group —HC═CH— and

D is the group

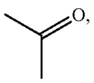

$R^1$ is hydrogen or an amino sugar of the abovementioned formula 1a.

2. The compound as claimed in claim 1, wherein in the case (12) that in the compound of the formula (I)

A-B is the group —HC═CH— or —HC═C($CH_3$)— and

D is the group

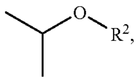

$R^1$ is an amino sugar of the formula 1a and $R^2$ is a sugar of the formula 2a, 2g or 2h or, in the case (13) that in the compound of the formula (I)

A-B is the group —HC═CH— and

D is as defined above, $R^1$ is an amino sugar of the formula 1a and $R^2$ is hydrogen or a sugar of the formula 2d, 2e, 2l, 2m or 2o or, in the case (14) that in the compound of the formula (I)

A-B is the group —HC═CH— or —HC═C($CH_3$)— and

D is as defined above, $R^1$ is hydrogen or an amino sugar of the formula 1b and $R^2$ is hydrogen or a sugar of the formula 2a or A-B, D and $R^1$ are as defined as in the case (11).

3. The compound as claimed in claim 1, wherein in the case (15) that in the compound of the formula (I)

A-B is the group —HC═CH— or —HC═C($CH_3$)— and

D is the group

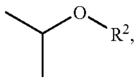

$R^1$ is an amino sugar of the formula 1a and $R^2$ is a sugar of the formula 2a or, in the case (16) that in the compound of the formula (I)

A-B is the group —HC═CH— and

D is as defined above, $R^1$ is an amino sugar of the formula 1a and $R^2$ is hydrogen or a sugar of the formula 2d, 2l or 2m or A-B, D and $R^1$ are as defined as in the case (11).

4. The compound as claimed in claim 1, wherein in the case (17) that in the compound of the formula (I)

A-B is the group —HC═CH— or —HC═C($CH_3$)— and

D is the group

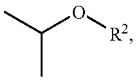

$R^1$ is an amino sugar of the formula 1a and $R^2$ is a sugar of the formula 2a or, in the case (18) that in the compound of the formula (I)

A-B is the group —HC═CH— and

D is as defined above, $R^1$ is hydrogen and $R^2$ is hydrogen.

5. The compound as claimed in claim 1, wherein in the compound of the formula (I)

A-B is the group —HC═CH—,

D is the group

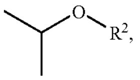

$R^1$ is an amino sugar of the formula 1a and $R^2$ is a sugar of the formula 2a, or in which in the compound of the formula (I)

A-B is the group —HC═CH— or —HC═C($CH_3$)—,

D is as defined above, $R^1$ is hydrogen and $R^2$ is a sugar of the formula 2a, or in which in the compound of the formula (I)

A-B is a group —HC═CH—,

D is as defined above, $R^1$ is hydrogen and $R^2$ is hydrogen.

* * * * *